(12) United States Patent
Berger et al.

(10) Patent No.: US 9,739,653 B2
(45) Date of Patent: Aug. 22, 2017

(54) FLOW SENSOR

(75) Inventors: Stefan Berger, Burgdorf (CH); Simon Zumbrunnen, Bern (CH); Philip Marmet, Worblaufen (CH); Philipp Haslebacher, Burgdorf (CH); Manfred Schär, Burgdorf (CH)

(73) Assignee: ReseaChem GmbH, Burgdorf (CH)

( * ) Notice: Subject to any disclaimer, the term of this patent is extended or adjusted under 35 U.S.C. 154(b) by 502 days.

(21) Appl. No.: 14/239,906

(22) PCT Filed: Aug. 21, 2012

(86) PCT No.: PCT/EP2012/066227
§ 371 (c)(1),
(2), (4) Date: Feb. 20, 2014

(87) PCT Pub. No.: WO2013/030034
PCT Pub. Date: Mar. 7, 2013

(65) Prior Publication Data
US 2014/0208833 A1    Jul. 31, 2014

(30) Foreign Application Priority Data

Aug. 26, 2011 (CH) ....................... 1398/11
Nov. 3, 2011 (CH) ....................... 1785/11

(51) Int. Cl.
*G01F 1/34* (2006.01)
*G01F 9/00* (2006.01)
(Continued)

(52) U.S. Cl.
CPC ............ *G01F 9/00* (2013.01); *G01F 1/34* (2013.01); *G01F 1/363* (2013.01); *G01F 1/42* (2013.01);
(Continued)

(58) Field of Classification Search
CPC ....................................................... G01F 1/34
(Continued)

(56) References Cited

U.S. PATENT DOCUMENTS 3,924,467 A * 12/1975 Takamura ................. G01F 1/36
73/861.59
6,463,810 B1 * 10/2002 Liu ........................... G01F 1/44
73/861
(Continued)

FOREIGN PATENT DOCUMENTS

DE      EP 0337092      * 10/1989
DE      19650115 C1      2/1996
(Continued)

OTHER PUBLICATIONS

English translation of the International Preliminary Report on Patentability from corresponding International Patent Application PCT/EP2012/066227, dated Mar. 13, 2014.
International Search Report and Written Opinion from corresponding International Patent Application PCT//EP2012/066227, dated Oct. 22, 2012.

Primary Examiner — Peter Macchiarolo
Assistant Examiner — Hoang Nguyen
(74) Attorney, Agent, or Firm — Brinks Gilson & Lione

(57) ABSTRACT

Proposed is a flow sensor (10), in particular for single use, having at least three measurement chambers (11, 15, 19), which are arranged one behind the other and are interconnected in each case by a flow resistance. At least two of the flow resistances have a different coefficient of pressure loss. A pressure measuring means (12, 16, 20) is provided for each measurement chamber, which pressure measuring means (12, 16, 20) is suitable for measuring the pressure in the measurement chamber. An electromagnetically actuatable valve arrangement (50) can be connected downstream of the flow sensor.

5 Claims, 3 Drawing Sheets

(51) Int. Cl.
*G01F 1/42* (2006.01)
*G01F 1/36* (2006.01)
*G01F 1/48* (2006.01)
*G01F 1/50* (2006.01)
*G01F 15/00* (2006.01)
*G01N 11/02* (2006.01)
*G01N 11/00* (2006.01)

(52) U.S. Cl.
CPC .................. *G01F 1/48* (2013.01); *G01F 1/50* (2013.01); *G01F 15/003* (2013.01); *G01F 15/005* (2013.01); *G01N 11/02* (2013.01); *G01N 2011/006* (2013.01)

(58) Field of Classification Search
USPC .......... 73/54.01, 54.11, 54.13, 54.14, 861.42
See application file for complete search history.

(56) References Cited

U.S. PATENT DOCUMENTS

| | | | |
|---|---|---|---|
| 8,136,414 B2* | 3/2012 | Steven | G01F 1/3209 73/861.63 |
| 2014/0013838 A1* | 1/2014 | Sawada | G01F 1/34 73/203 |
| 2014/0200836 A1* | 7/2014 | Lee | G01F 1/34 702/47 |

FOREIGN PATENT DOCUMENTS

| EP | 0166502 A1 | 2/1986 |
|---|---|---|
| EP | 0337092 A2 | 10/1989 |

\* cited by examiner (a)

(b)

(c)

(d)

FLOW SENSOR

This application is the U.S. National Stage under 35 U.S.C. §371 of International Patent Application PCT/EP2012/066227, filed Aug. 21, 2012, which claims the priority of CH 01398/11, filed Aug. 26, 2011 and CH 01785/11 filed Nov. 3, 2011. These applications are incorporated by reference herein in their entirety.

TECHNICAL FIELD

The invention relates to flow sensors having at least three measurement chambers which are arranged one behind the other and are fluidically connected by flow resistors, wherein at least two of the flow resistors have a different coefficient of pressure loss. The invention further relates to metering devices comprising such flow sensors, and to methods for determining a volume flow and/or a viscosity of a fluid by means of such flow sensors.

PRIOR ART

When cultivating micro-organisms, it is important to feed culture media exactly and with given metering rates to the reaction vessel. For large bioreactors (>500 L, metering rate >1 kg/h), metering pumps or scales are used for this purpose.

In the international application PCT/EP2011/052545 of the applicant, an advantageous dosing system for metered addition of fluids into reaction vessels is described. The content of the cited application shall hereby be deemed by reference to be an integral part of the present specification. In the mentioned metering system, the metered addition into reaction vessels is carried out drop by drop by means of a suitable metering device, for example, an electromagnetically actuated precision valve.

The required metering accuracy is achieved in that the differential pressure in the metering unit is controlled very accurately in that, in addition, the actual metering rate is monitored via a metering rate determination means such as a scale or a flow sensor, and the differential pressure is readjusted accordingly. Very precise controlling of the differential pressure is necessary, among other things, because the drop size resulting from a certain opening period of the valve and a certain fluid pressure is dependent on the viscosity of the fluid and therefore also on the temperature.

Furthermore, in this metering system, the metering device and the metering rate determination means are arranged separately and not necessarily in a spatially constant position relative to one another, which, due to the resulting undefined hydrostatic pressure differences, influences the differential pressure control. In order to ensure exact metering rates over a longer period, these effects have to be taken into account, if necessary. This results in a complex control.

A flow meter known from the prior art for measuring small flow rates in the microliter range is, for example, the so-called MEMS flow sensor of the company Seyonic, CH-2000 Neuchatel, Switzerland. This flow sensor is used in pipetting systems and comprises a measuring channel, a piezo-resistive pressure sensor and a temperature sensor. The disadvantage of this sensor is that due to dynamic viscosity influences, the measured flow rates are dependent on temperature, and in addition to the flow rate, the temperature or, respectively, the viscosity of the fluid to be measured also has to be taken into account.

Accordingly, it is necessary to calibrate the flow sensor prior to the measurement.

In the dissertation "Durchflusssensoren aus Kunststoff für sehr kleine Volumenstrome auf Basis des AMANDA-Verfahrens" of Dipl.Ing Dirk Maria Dittmann, Forschungszentrum Karlsruhe GmbH, Karlsruhe, 2002, a temperature-dependent flow sensor is presented. In this flow sensor, two measurement chambers are connected one behind the other, wherein in each of the two measurement chambers, an elastic membrane having a center hole is arranged. The two membranes arranged one behind the other are arranged to be movable in the measurement chamber, have a different thickness, and function as flow resistors. The fluid volume flow to be measured enters the first measurement chamber, passes the center hole of the first membrane, flows into the second measurement chamber and passes the center hole of the second membrane. The pressure loss at each membrane is determined by electronically measuring the elongation of the membrane, and by determining the pressure difference from this elongation. The influence that the first membrane exerts on the second membrane when the fluid flows through is not taken into account. The coefficients $\zeta 1$ and $\zeta 2$ of pressure loss for the flow through the membrane openings are set equal. By connecting the two membranes, which serve as flow resistors, one behind the other, it is intended to measure the fluid volume flow independently of the viscosity, and therefore independently of the temperature. The derivation of the theoretical formula for the correlation of the temperature-independent flow measurement is explained in the aforementioned dissertation, starting on page 26. The content of this document shall hereby be deemed by reference to be an integral part of the present specification.

In the dissertation "Durchflussmessung kleinster Flussigkeitsmengen" of Dipl. Ing. Götz Schnell, Darmstadt, 1995, different measuring methods to be used for measuring the flow rate of extremely small amounts of liquid were analyzed. In chapter 8.4 of the dissertation "Durchflussmessung durch Messen des Druckabfalls in geraden Rohren", the derivation of the theoretical formula for pressure loss across a channel-shaped flow resistor is illustrated. The content of this chapter shall hereby be deemed by reference to be an integral part of the present specification. The dissertation discusses different possible solutions for reducing the influence of throttling the flow as proportion of the pressure drop across a tube section so as to enable a more exact measurement. In the proposed measuring principle, a straight tube section is configured such that two capillary tubes are arranged closely one behind the other. The first capillary tube serves for forming the flow profile and therefore for reducing the pressure drop caused by the throttling when the flow enters the second capillary tube. The second capillary tube represents a measuring capillary tube via which the pressure drop is measured. The total pressure drop across the tube is composed of the throttling proportion that is reduced as far as possible and of the proportion of friction. This frictional pressure is a viscosity- and/or temperature-dependent variable. The configuration proposed in the dissertation allows minimizing the pressure proportion of the throttling of the fluid to be measured in order to substantially measure only the frictional effect. The measured pressure drop is furthermore dependent on the viscosity and the temperature.

In biotechnology, very high requirements are placed on sterility. All components have to be sterilized (e.g., autoclaved) prior to a new test or batch. In order to avoid this and to reduce the efforts for cleaning and the necessary quality inspection while maintaining the same high quality, single-use components or disposables are increasingly used. They are available in sterile condition, are fitted in and are subsequently disposed of. Up to now, precise metering systems are not available as single-use components, which renders their use as single-use components uneconomical.

REPRESENTATION OF THE INVENTION

It is an object of the invention to provide a flow sensor which can be produced cost-effectively, preferably as a single-use product, and by means of which small amounts of fluid can be measured precisely.

Another object of the invention is to provide a flow sensor by means of which a flow rate of a fluid can be measured without knowing the exact viscosity and/or temperature of the fluid, or which does not require a preceding calibration.

Likewise, it is an object of the invention to provide a metering device which can be produced as a cost-effective single-use product and by means of which small amounts of fluids can be metered precisely. Advantageously, a metering device according to the invention shall allow measuring the volume of an individual drop that is added by metering.

It is another object of the invention to provide a method which makes it possible to measure a volume flow of a fluid without knowing the viscosity and/or the temperature of the fluid, and/or with a preceding calibration.

This and other objects are achieved by a flow sensor, a metering device and a method according to the independent claims. Preferred embodiments of the invention are specified in the dependent claims.

A flow sensor according to the invention comprises at least three measurement chambers which are arranged one behind the other and are interconnected in each case by a flow resistor. At least two of the flow resistors have a different coefficient of pressure loss. For each measurement chamber, a pressure measuring means is provided which is suitable for measuring the pressure p in the respective measurement chamber.

The flow sensor according to the invention is in particular provided for single use.

In an advantageous embodiment of the flow sensor according to the invention, three measurement chambers are arranged serially one behind the other. Particularly advantageous, the middle one of the three measurement chambers has a smaller volume than the two other measurement chambers.

Due to this arrangement it can be achieved to bring an outlet opening of the first flow resistor as close as possible to an inlet opening of the second flow resistor. The first flow resistor influences the subsequent flow resistor such that the exiting fluid flow cannot spread out completely in the second measurement chamber and thus can partially maintain its flow profile. Since the fluid flow is virtually directed towards the second friction channel, the throttling effect of the inlet opening decreases accordingly, and the coefficient of pressure loss is lower.

The flow resistors are preferably configured such that each them has a friction channel with a given length L1, L2 and a given cross-sectional area A1, A2. The lengths L1 and L2 and/or the cross-sectional areas A1 and A2 of the friction channels can be selected to be equal or different. In an advantageous embodiment, the cross-sectional areas A1, A2 have a value between 0.03 and 0.3 mm$^2$; alternatively or additionally, the length L1, L2 of the friction channels is less than 2 mm.

In order to be able to produce the flow sensor in a cost-effective manner, pressure sensors are needed that are inexpensive, but nevertheless precise. Suited as pressure measuring means in a flow sensor according to the invention are, for example, semiconductor pressure sensors, in particular the pressure sensors MPX2300DT1 and MPX2301DT1 of the company Freescale, Austin, Tex., USA (http://www.freescale.com).

Due to the simple construction of the sensor, the flow sensor according to the invention can be injection molded, preferably as one piece, and thus can be produced as cost-effectively as possible.

In a particularly advantageous embodiment of the invention, the flow sensor has a valve device, preferably an electromagnetically actuatable valve, that is arranged downstream of the last measurement chamber. With this advantageous arrangement it is achieved to measure the flow rate of a fluid to be metered as close as possible at the entry into the valve device and optionally to readjust the metering device if a metering rate set by the user does not correspond to the actual metering rate.

Through the arrangement according to the invention of the flow sensor having the valve device and by using a suitable valve device, it is achieved, among other things, to meter individual drops of the fluid and thereby to measure or check the volume of each individual drop added by metering. These values can also be recorded, for example for quality control.

A metering device according to the invention for metering fluids comprises a feed channel for feeding the fluid to be metered, a flow sensor according to the invention as discussed above for determining the volume flow through the sensor, wherein the feed channel is fluidically connected to the first measurement chamber of the flow sensor, and a valve device for metering the fluid, preferably an electromagnetically actuatable valve, wherein the last measurement chamber is connected to the inlet of the valve device.

In a method according to the invention for measuring a volume flow $[V/t]_M$ and/or a viscosity $\eta_M$ of a fluid, a flow sensor according to the invention as discussed above is provided, and for at least two flow resistors of the flow sensor having different coefficients $\zeta$ of pressure loss, a family of characteristics from a plurality of isobaric characteristics is provided, wherein the mentioned isobaric characteristics represent volume flow/viscosity value pairs, which cause a certain differential pressure at the corresponding flow resistor. Across the corresponding at least two flow resistors, the differential pressures $\Delta p$ are determined in that the pressures in the corresponding measurement chambers are measured by means of the pressure measuring means, and the differential pressures are calculated therefrom. In the respective families of characteristics, the determined at least two differential pressures are assigned the corresponding isobaric characteristic having the same differential pressure, and the intersection of the assigned at least two isobaric characteristics is determined. From this determined intersection, subsequently, the associated volume flow $[V/t]_M$ and/or the associated viscosity $\eta_M$ is determined.

According to theory, the pressure drop $\Delta p$ between two measurement chambers which are connected by a friction channel with the radius $r_R$ and the length $l_R$ is: $\Delta p = [\zeta \rho/(\pi^2 r_R^4)][V/t]^2 + [8\eta l_R/(\pi r_R^4)][V/t]$. The coefficient $\zeta$ of pressure loss takes into account the flow profile at the inlet in the friction channel. $\rho$ is the density of the fluid. This three-dimensional function can be converted such that with $\zeta$, $\rho$, $l_R$, $r_R$ as fix parameters, the pressure drop $\Delta p$ can be represented as three-dimensional function of the volume flow $[V/t]$ and the viscosity $\eta$. From this function, characteristics for a certain $\Delta p$ can be calculated.

Instead of determining the families of characteristics with mathematical models, they can also be obtained through numerical simulations. Experimental determination of a multiplicity of measurement value triplets and the subsequent numerical interpolation of a three-dimensional function are also advantageous.

Such a method according to the invention thus allows determining a flow rate or volume flow without the need of knowing the viscosity. The viscosity is even obtained during the flow measurement as an additional measurement value.

In an advantageous variant of such a method, the isobaric characteristics of the families of characteristics of the flow resistor are extrapolated from suitable characteristic values, preferably from characteristic values determined through measurements.

Additionally or alternatively, it is possible with such a method according to the invention to determine the differential pressure as a function of time. This allows a precise integration of individual drop volumes, for example.

Due to the underlying physical effects, families of characteristics apply only to certain fluid densities p. Thus, the density of the fluid has to be known. However, the density is usually known or can at least be determined in a simple manner. Alternatively, four-dimensional functions can also be used, with the density being an additional function parameter. Therefrom, three-dimensional isobaric characteristic areas can then be determined. Accordingly, for unique determination of the volume flow (as well as the viscosity and the density), three intersecting isobaric characteristic areas are required, thus three flow resistors having different coefficients of pressure loss are also required.

BRIEF DESCRIPTION OF THE FIGURES

The invention is explained below in greater detail by means of exemplary embodiments with reference to the drawings.

WAYS FOR IMPLEMENTING THE INVENTION

Figure 1:
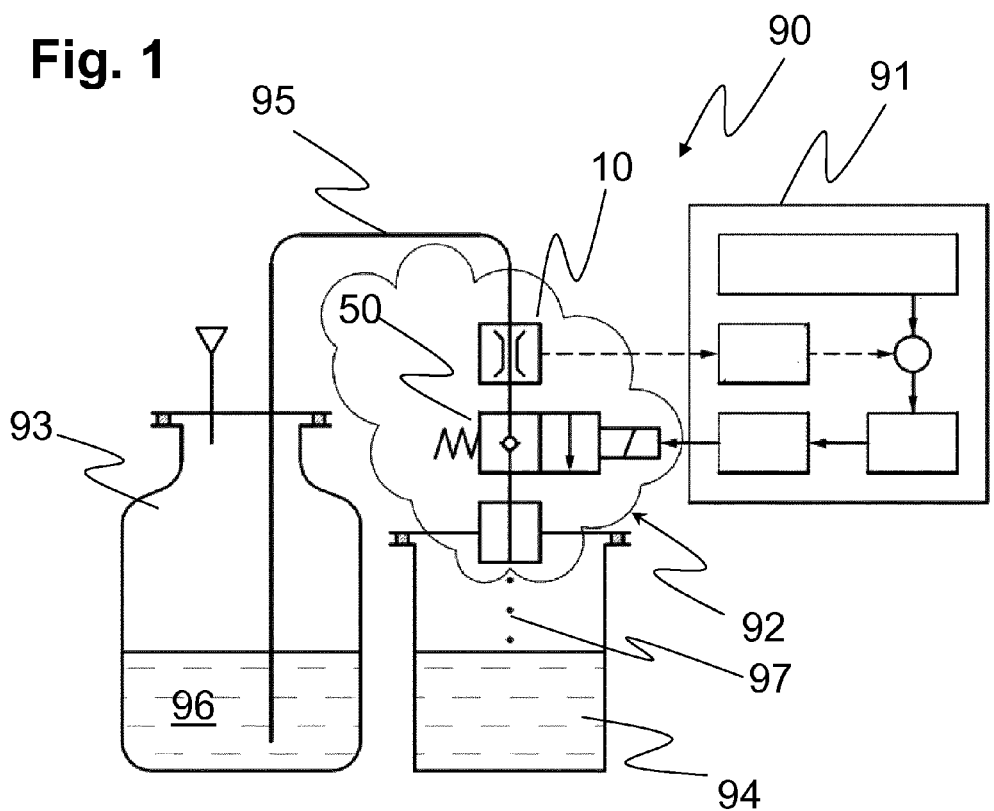
FIG. 1 shows schematically the use of a flow sensor according to the invention in a metering system.

In a preferred embodiment of the invention according to FIG. 1, the flow sensor 10 according to the invention is used in a metering system 90, for example, for a bioreactor 94. The fluid 96 to be metered is transported from a reservoir 93 via a transfer line 95 to a metering device 92 which comprises the flow sensor 10 according to the invention and a valve device 50. By means of the metering valve 50, the fluid to be metered is fed in the form of individual drops 97 to the bioreactor 94. The flow sensor 10 and the metering valve 50 are advantageously formed as one piece, preferably as a disposable unit.

The flow sensor 10 according to the invention measures the current metering rate directly at the metering valve 50. A control device 91 controls the opening time and/or the frequency of the metering valve 50 based on a target metering rate preset by the user and on the second actual metering rate measured by the flow sensor 10 according to the invention so that the actual metering rate corresponds to the desired metering rate.

Figure 2:
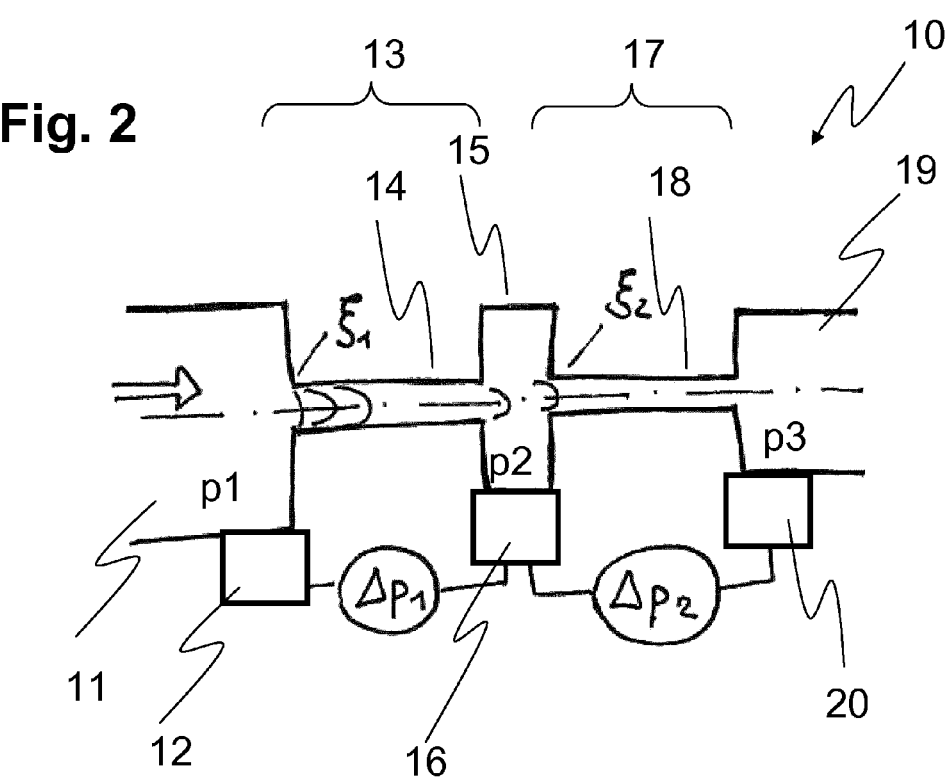
FIG. 2 shows a schematic illustration of the flow sensor according to the invention in a cross-sectional view.

FIG. 2 shows greatly simplified a flow sensor 10 according to the invention with a first measurement chamber 11, a second measurement chamber 15 and a third measurement chamber 19. The measurement chambers are fluidically interconnected by a first flow resistor 13 and a second flow resistor 17. In the illustrated particularly advantageous embodiment, the flow resistors 13 and 17 are formed by a first 14 and a second 18 friction channel having a cross-sectional area A1, A2 and a length L1, L2. The coefficients $\zeta$ of pressure loss for the flow resistors are different. The second measurement chamber 15 is smaller, in particular shorter, than the first measurement chamber 11, for example. The measurement chamber 15 is configured such that an outlet opening of the first friction channel 14 is arranged at a suitably small distance from an inlet opening of the second flow channel 18. As a result, the flow profile has no time to uniformly spread out in the measurement chamber. The fluid flow is directed, as it were, towards the inlet opening. As a result, the throttling effect of the inlet opening decreases with respect to the value that is theoretically to be expected due to the geometry. This results in different coefficients of pressure loss for the two flow resistors 13 and 17.

Optimum geometries for the measurement chambers and friction channels can be determined in dependence on a preferred range of viscosity, density and volume flow by means of mathematical models and/or by numeric simulations. Optimizing can take place in particular with regard to the accuracy of the determination of the volume flow according to the method according to the invention.

For each measurement chamber, in each case one pressure measuring means 12, 16, 20 is provided. In a preferred embodiment, this is, for example, a disposable pressure sensor of the company Freescale Semiconductor, http://Freescale.com, of the type MPX2300DT1 and/or the type MPX2301DT1. The differential pressures $\alpha p1$ and $\alpha p2$ are determined in that the difference is determined from the pressure values p1, p2, p3 in the measurement chambers.

Figure 3:
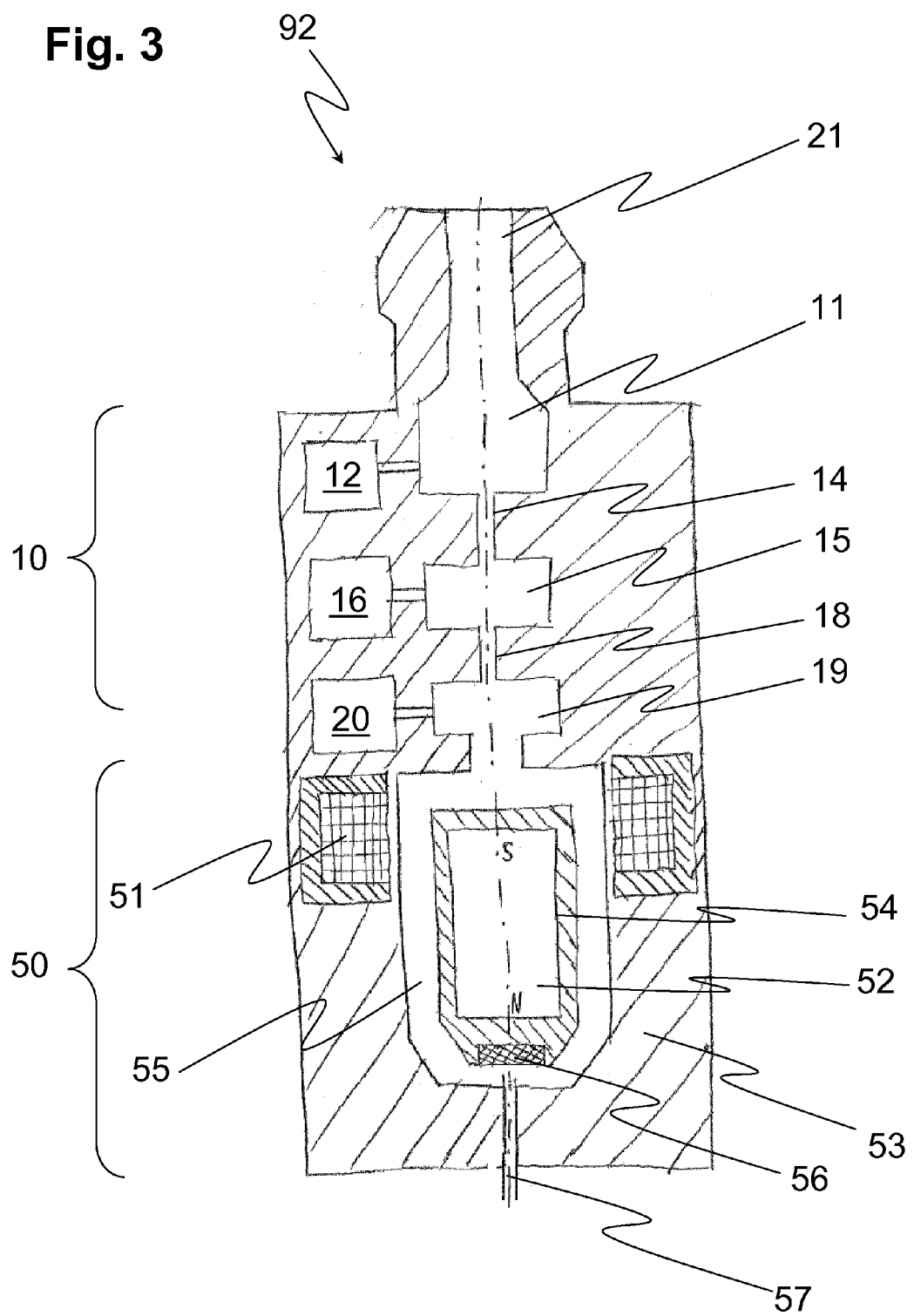
FIG. 3 shows schematically a metering device according to the invention with a flow sensor according to the invention and a valve device.

FIG. 3 shows a flow sensor 10 according to the invention as part of a metering device according to the invention, wherein the flow sensor is fluidically connected to a valve device 50. In the embodiment shown, this is an electromagnetically actuatable valve. In valves of this kind, a magnetic armature 52 is displaced with a given clock frequency by a magnetic coil 51 in a valve chamber 55, and thereby an outlet opening 57 of a valve nozzle is opened during a period that also can be determined, and is subsequently closed again. In this manner it is possible to specifically feed a certain volume of the pressurized fluid into the outlet nozzle 57 and thus to dispense at the end of the nozzle a drop having a certain volume. The armature 52 of the metering valve 50 is preferably arranged in a capsule that protects the armature against aggressive media, for example, diluted acids.

The flow sensor 10 that is arranged upstream of the metering valve 50 is the same flow sensor as the one described in FIG. 2. In the preferred embodiment according to FIG. 3, the flow sensor 10 and the metering valve 50 are formed as one piece.

Figure 4:
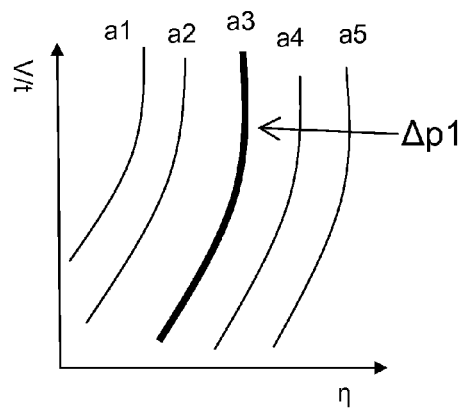
FIG. 4 shows schematically (a) a first family of characteristics of a first flow resistor, with an isobaric characteristic belonging to a first measured pressure difference, (b) a second family of characteristics of a second flow resistor, with an isobaric characteristic belonging to a second measured pressure difference, (c) the determination of the intersection of the first and second isobaric characteristics, and based thereon the determination of the volume flow and the viscosity; and (d) the determination of the volume flow and the viscosity in an embodiment variant with three measured pressure differences and three isobaric characteristics.
Figure 4:
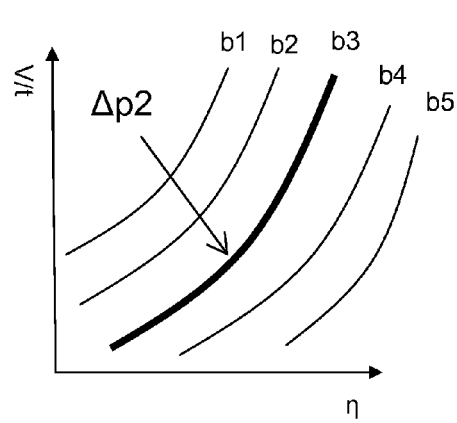
Figure 4:
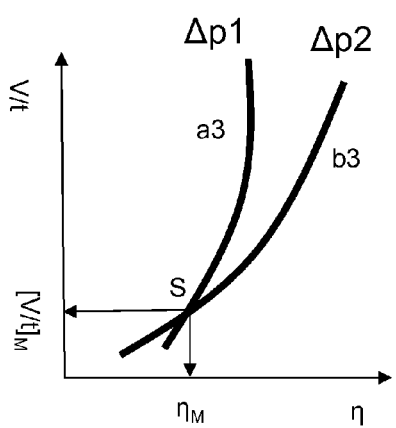
Figure 4:
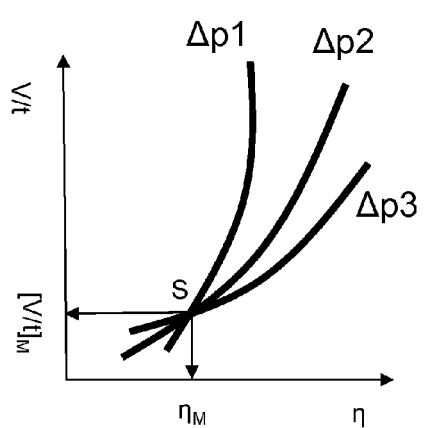

For a first flow resistor, a family of characteristics is created which illustrates the relation between volume flow, viscosity and pressure drop at the flow resistor. In FIG. 4(a), such a family of characteristics is symbolically illustrated, with a plurality of characteristics a1-a5 representing different pressure differences across the flow resistor. The same is done for a second flow resistor (FIG. 4(b)). However, since this second flow resistor has a different coefficient of pressure loss, the characteristics b1 to b5 are tilted compared to those of the first flow resistor. If now the actual pressure differences Δp1, Δp2 are determined experimentally, the corresponding characteristics a3, b3 in the respective families of characteristics can be assigned to said actual pressure differences. Since the viscosity of the fluid, of course, remains unchanged, and the volume flow has to be identical due to the experimental setup, a value pair from volume flow [V/t]M and viscosity ηM can be clearly determined by intersecting the two characteristics a3, b3 (FIG. 4(c)).

FIG. 4(d) shows a variant in which three differential pressures are measured across three flow resistors having different coefficients of ζ pressure loss, and accordingly, three characteristics are intersected. The additional measurement increases the measuring accuracy.

REFERENCE LIST

10 Flow sensor
11 First measurement chamber
12 First pressure measuring means
13 First flow resistor
14 First friction channel
15 Second measurement chamber
16 Second pressure measuring means
17 Second flow resistor
18 Second friction channel
19 Third measurement chamber
29 Third pressure measuring means
21 Feed channel
50 Valve device, metering valve
51 Magnetic coil
52 Magnet armature
53 Valve seat
54 Valve part
55 Valve chamber
56 Sealing element
57 Outlet nozzle
90 Metering system
91 Control device
92 Metering device
93 Reservoir
94 Bioreactor
95 Transfer line
96 Fluid
97 Drop, volume added by metering
Δp1, Δp2, Δp3 Differential pressure
p1, p2, p3 Pressure in measurement chamber
ζ1, ζ2 Coefficients of pressure loss
a1 . . . a5, b1-b5 Isobaric characteristics
S Intersection

The invention claimed is:

1. A method for measuring a volume flow or viscosity of a fluid, comprising:
providing a flow sensor with at least three measurement chambers which are arranged one behind the other and are fluidically interconnected by a plurality of flow resistors, wherein at least two of the plurality of flow resistors have a different coefficient of pressure loss, wherein a pressure sensor is provided for each measurement chamber;
providing a family of characteristics from a plurality of isobaric characteristics, wherein the isobaric characteristics represent volume flow and viscosity value pairs, which cause a certain differential pressure across the corresponding flow resistor;
determining at least two differential pressures across the corresponding at least two of the plurality of flow resistors in that the pressures in the corresponding measurement chambers are measured by the pressure sensors;
assigning the determined at least two differential pressures to the corresponding isobaric characteristic having the same differential pressure in the respective families of characteristics;
determining the intersection of the assigned at least two isobaric characteristics;
determining the associated volume flow or the associated viscosity from the determined intersection.

2. The method according to claim 1, wherein the isobaric characteristics of the families of characteristics of the at least two of the plurality of flow resistors are extrapolated from suitable characteristic values.

3. The method according to claim 1, wherein the differential pressures are determined as a function of time.

4. The method according to claim 1, wherein the isobaric characteristics of the families of characteristics of the flow resistors are extrapolated from characteristic values determined through measurements.

5. The method according to claim 2, wherein the differential pressures are determined as a function of time.

* * * * *